United States Patent
Kajisa et al.

(10) Patent No.: US 11,630,077 B2
(45) Date of Patent: Apr. 18, 2023

(54) HIGH-SENSITIVITY BIOSENSOR

(71) Applicant: Provigate Inc., Tokyo (JP)

(72) Inventors: Taira Kajisa, Tokyo (JP); Yoshiyuki Yanagimoto, Tokyo (JP)

(73) Assignee: Provigate Inc., Tokyo (JP)

( * ) Notice: Subject to any disclaimer, the term of this patent is extended or adjusted under 35 U.S.C. 154(b) by 827 days.

(21) Appl. No.: 16/487,016

(22) PCT Filed: Feb. 19, 2018

(86) PCT No.: PCT/JP2018/005683
§ 371 (c)(1),
(2) Date: Oct. 15, 2019

(87) PCT Pub. No.: WO2018/155369
PCT Pub. Date: Aug. 30, 2018

(65) Prior Publication Data
US 2020/0049654 A1  Feb. 13, 2020

(30) Foreign Application Priority Data

Feb. 21, 2017 (JP) .............................. JP2017-029684

(51) Int. Cl.
*G01N 27/414* (2006.01)
*G01N 27/327* (2006.01)
*G01N 27/416* (2006.01)

(52) U.S. Cl.
CPC ..... *G01N 27/4145* (2013.01); *G01N 27/3275* (2013.01); *G01N 27/416* (2013.01)

(58) Field of Classification Search
None
See application file for complete search history.

(56) References Cited

U.S. PATENT DOCUMENTS

2006/0016699 A1  1/2006 Kamahori et al.
2012/0270964 A1  10/2012 Piletsky et al.
(Continued)

FOREIGN PATENT DOCUMENTS

CN        104677962      6/2015
DE     102004035245 A1   2/2006
(Continued)

OTHER PUBLICATIONS

J.A. Ribeiro, et al., "Electrochemical sensors and biosensors for determination of catecholamine neurotransmitters: A review", Talanta, 160: p. 653-679, Nov. (Year: 2016).*

(Continued)

*Primary Examiner* — J. Christopher Ball
(74) *Attorney, Agent, or Firm* — Myers Bigel, P.A.

(57) ABSTRACT

The object of the invention is to increase the detection specificity of biosensors. The present invention provides a biosensor characterized in that it comprises an identifier substance that can bind to a detection target substance and an electrode that takes the charge of said identifier substance, wherein the biosensor detects the change in the charge density of said electrode generated by the binding of said detection target substance with said identifier substance, the surface of said electrode is coated with polycatecholamine, all or a part of said electrode surface coated with polycatecholamine further has a polymer layer formed thereon which has a molecular imprint having a structure complementary to the molecular structure of the detection target substance formed therein, said polymer layer comprises said identifier substance, and said polymer layer is an ultrathin film layer.

19 Claims, 13 Drawing Sheets

(56) References Cited

U.S. PATENT DOCUMENTS

2012/0293160 A1 11/2012 Koto et al.
2016/0169835 A1 6/2016 Sakata et al.

FOREIGN PATENT DOCUMENTS

| JP | S6080754 A | 5/1985 |
|---|---|---|
| JP | 2007313400 | 12/2007 |
| JP | 2012242172 | 12/2012 |
| JP | 2012246163 | 12/2012 |
| JP | 2013512324 | 4/2013 |
| JP | 2016038384 | 3/2016 |
| WO | 2012124800 | 9/2012 |
| WO | 2017163715 | 9/2017 |

OTHER PUBLICATIONS

Extended European Search Report corresponding to European Patent Application No. 18757565.9 (17 pages) (dated Dec. 3, 2020).
Fowler, Steven Andrew "The Development of Sensors for the Detection of Clinically Relevant Substances Using Molecular Imprinting" PhD Thesis, Cranfield University (194 pages) (2009).
Iskierko et al. "Extended-gate field-effect transistor (EG-FET)with molecularly imprinted polymer (MIP) film for selective inosinedetermination" Biosensors and Bioelectronics, 74:526-533 (2015).
Iskierko et al. "Molecularly imprinted polymer based extended-gate field-effect transistor chemosensors for phenylalanine enantioselective sensing" Journal of Materials Chemistry C, 5(4):969-977 (2017).
Lakshmi et al. "Electrochemical Sensor for Catechol and Dopamine based on a catalytic molecularly imprinted Polymer-Conducting Polymer Hybrid Recognition Element" Analytical Chemistry, 81(9):3576-3584 (2009).
Tamboli et al. "Hybrid Synthetic Receptors on MOSFET Devices for Detection of Prostate Specific Antigen in Human Plasma" Analytical Chemistry, 88(23):11486-11490 (2016).
Vaselbehagh et al. "Improved antifouling of anion-exchange membrane by polydopamine coating inelectrodialysis process" Desalination, 332(1):126-133 (2014).
Yang et al. "Molecularly imprinted electrochemical sensor based on bioinspired Au microflowers for ultra-trace cholesterol assay" Biosensors and Bioelectronics, 92:748-754 (2017).
English Translation of the International Search Report and the Written Opinion of the International Searching Authority corresponding to International Patent Application No. PCT/JP2018/005683 (10 pages) (dated May 22, 2018).
Kajisa et al. "Characterization of ion-sensitive extended-gate field effect transistor coated with functional self-assembled monolayer" Japanese Journal of Applied Physics, 54:04DL06-1-04DL06-5 (2015).
Nakamura et al. "Preparation of Glucose Dehydrogenase and Quinones-immobilized Bioanode by Polydopamine Coating" Lecture Abstract of 82nd Conference of the Electrochemical Society of Japan, non-official translation, 2M09, p. 663 (2015).
Toma et al. "Polydopamine thin films as protein adhesion layer for surface plasmon enhanced fluorescence biosensors" The 63rd JSAP Spring Meeting, non-official translation (2016).
Wan et al. "Direct immobilization of antibodies on a bioinspired architecture as a sensing platform" Biosensors and Bioelectronics, 26:2595-2600 (2011).
European Examination Report corresponding to EP 18757565.9; dated Nov. 24, 2022 (24 pages).
Yoshimi, et al., "Development of an enzyme-free glucose sensor using the gate effect of a molecularly imprinted polymer", Journal of Artificial Organs, 12(Article No. 264), 2009, 264-270.

\* cited by examiner

[Figure 1]
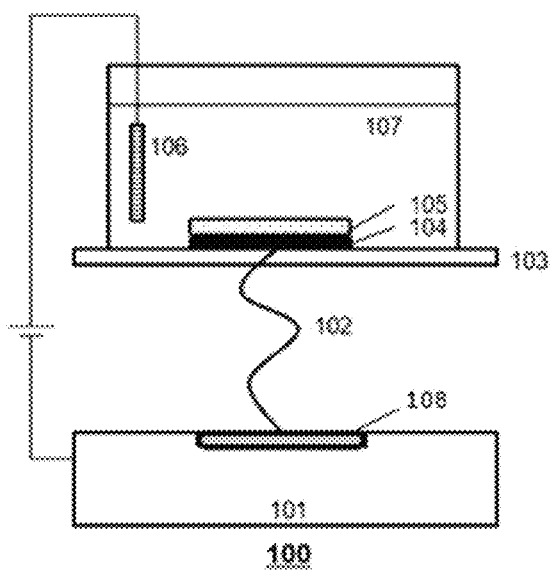
100: Gate electrode extended ion-sensitive sensor
101: Electric signal detector (MOSFET)
102: Electric wiring
103: Base plate
104: Ion-sensitive electrode (gold electrode)
105: Polycatecholamine thin film layer
106: Reference electrode
107: Buffer
108: Gate electrode

[Figure 2]
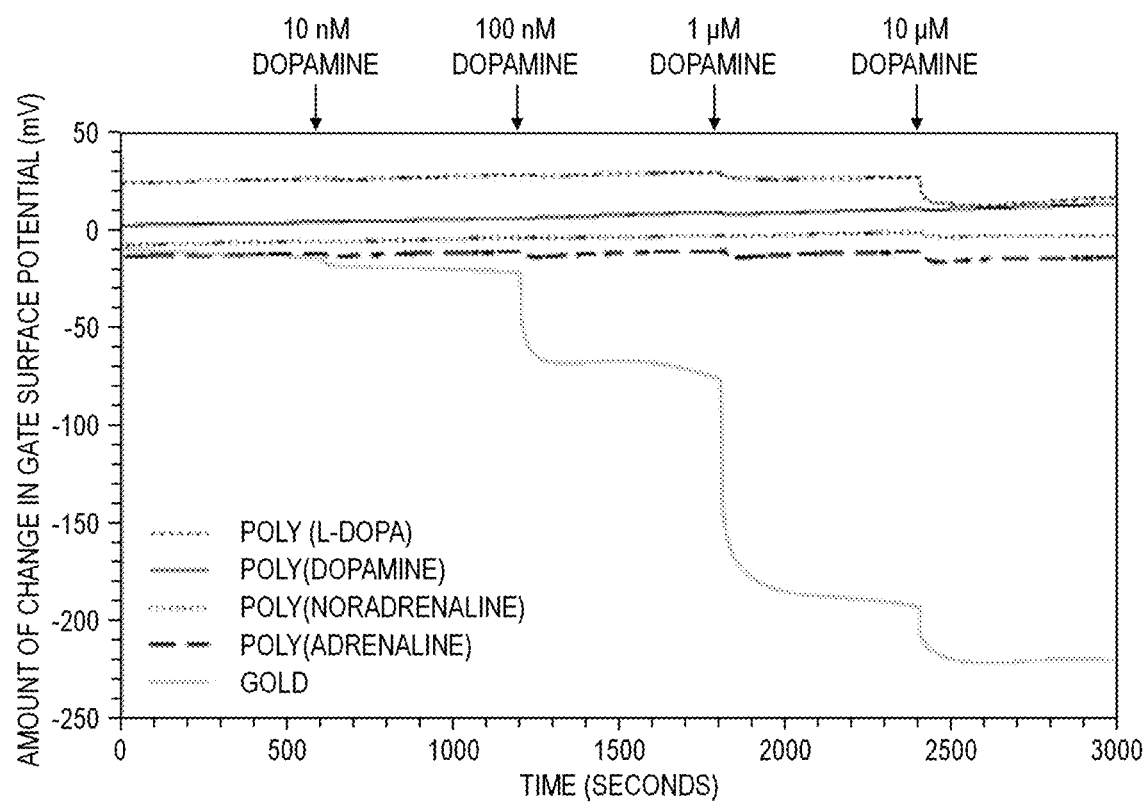

[Figure 3]
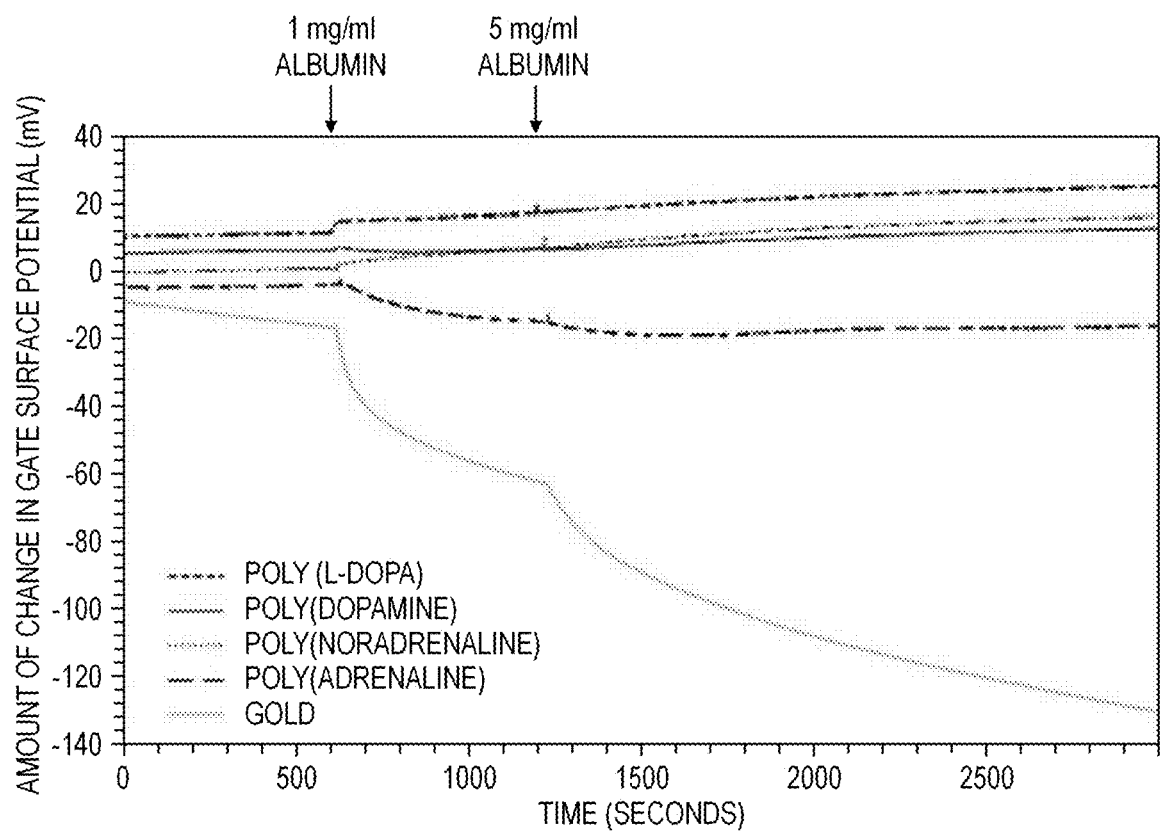

[Figure 4]
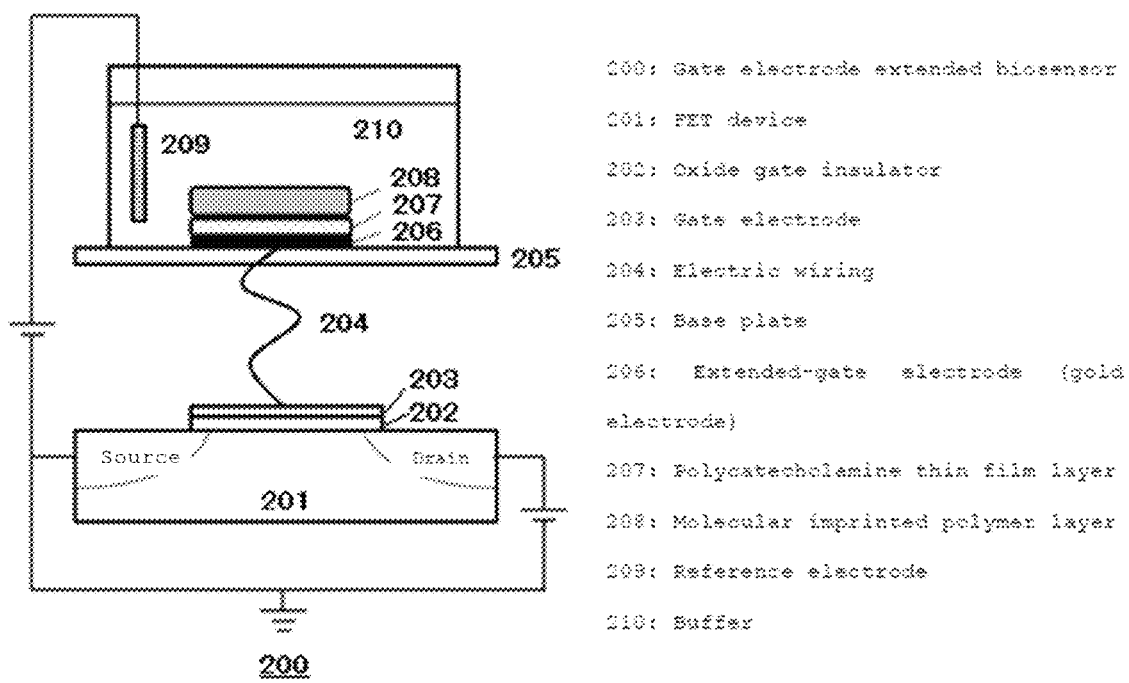
200: Gate electrode extended biosensor
201: FET device
202: Oxide gate insulator
203: Gate electrode
204: Electric wiring
205: Base plate
206: Extended-gate electrode (gold electrode)
207: Polycatecholamine thin film layer
208: Molecular imprinted polymer layer
209: Reference electrode
210: Buffer

[Figure 5]
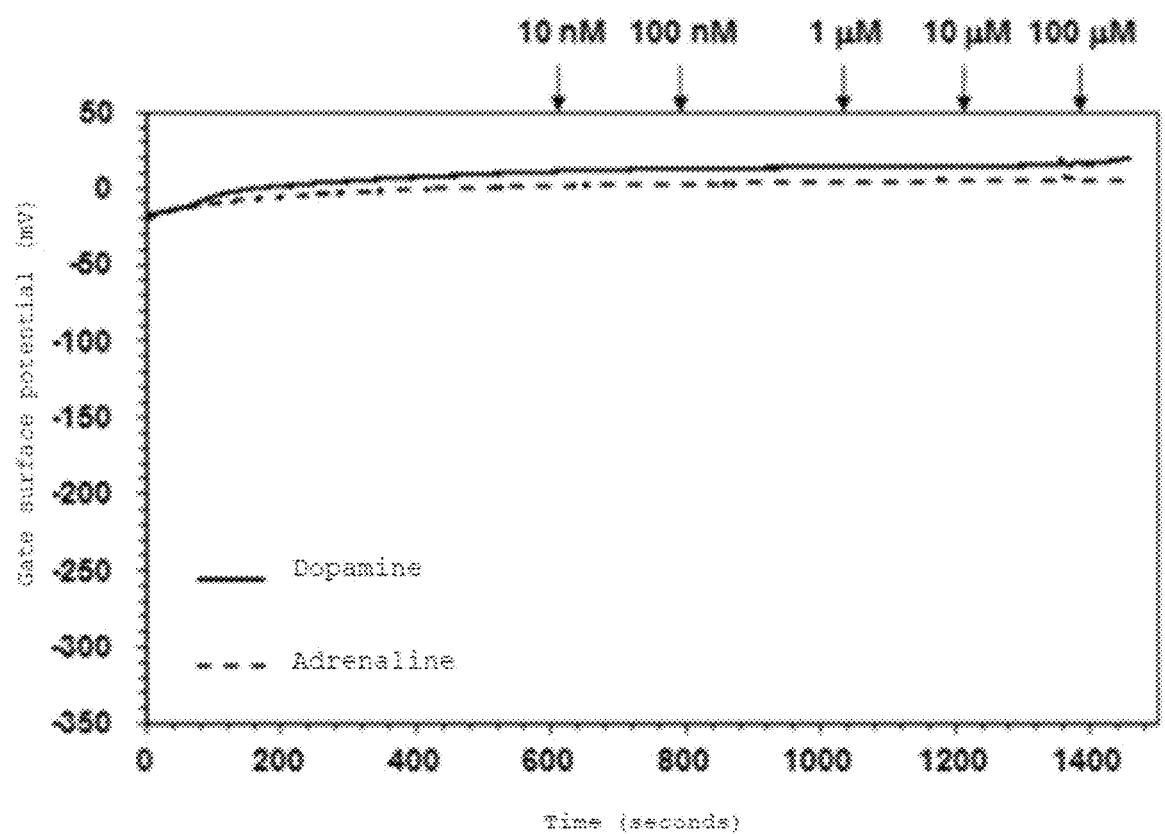

[Figure 6]
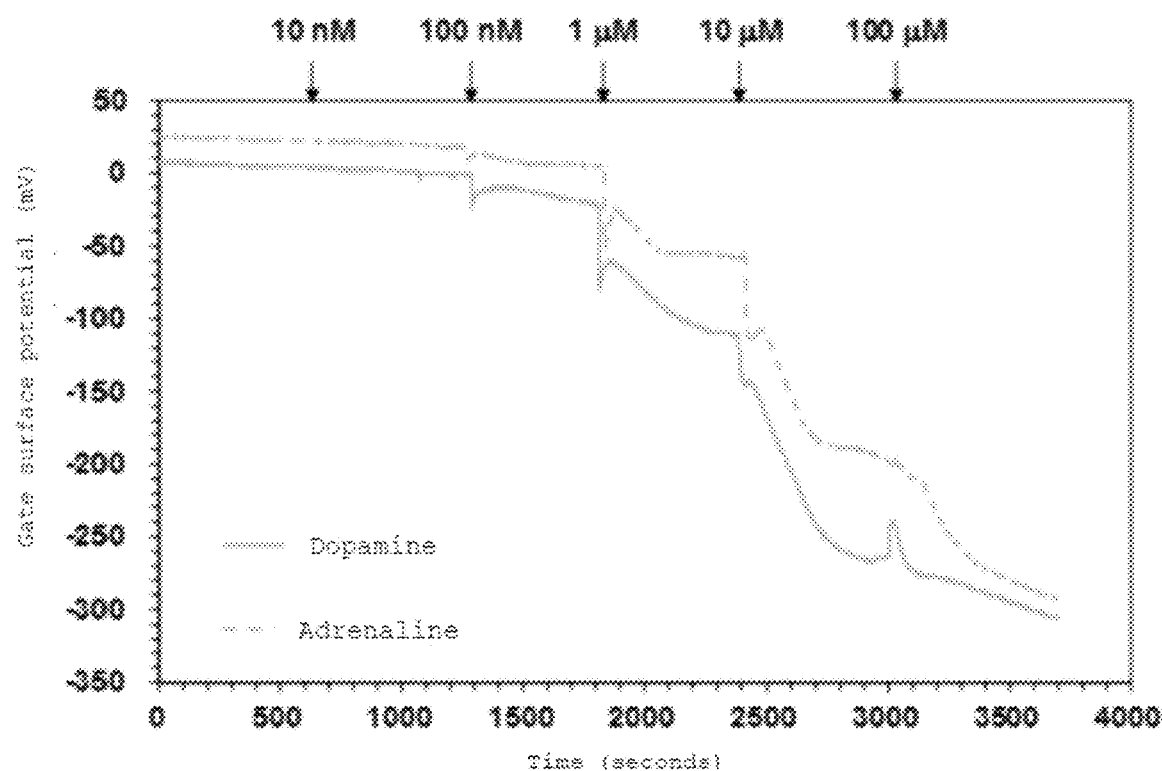

[Figure 7]
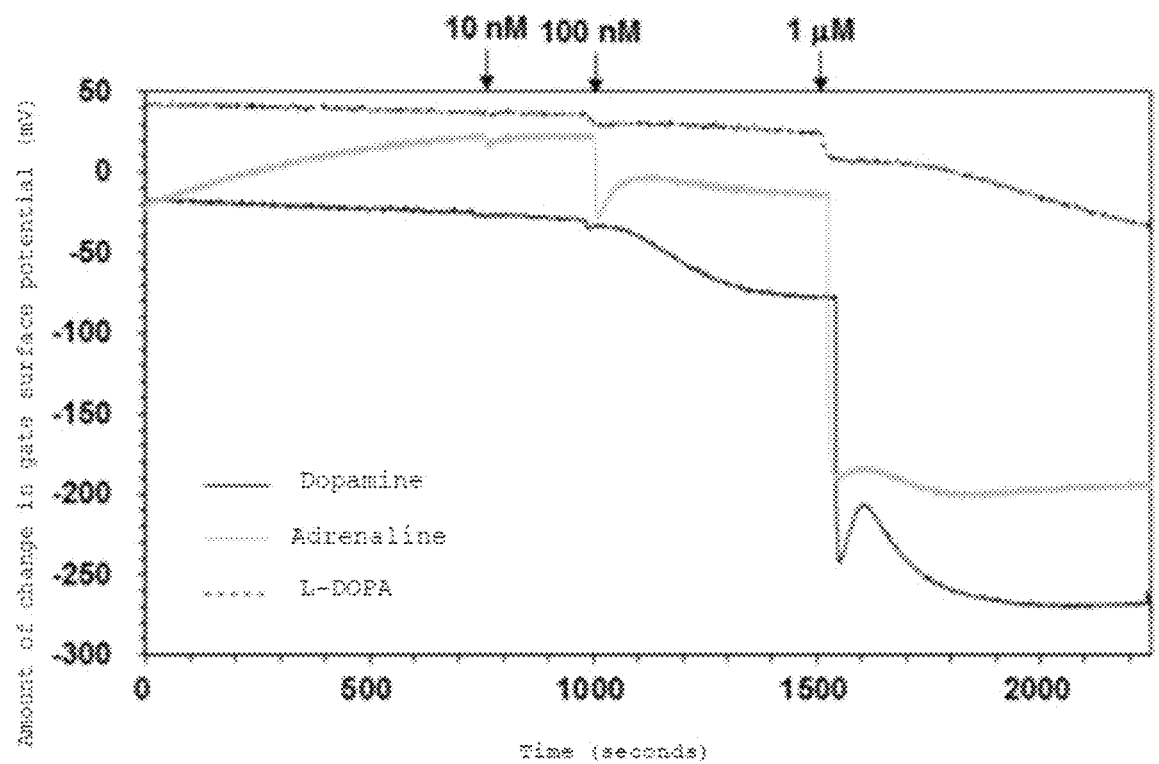

[Figure 8]
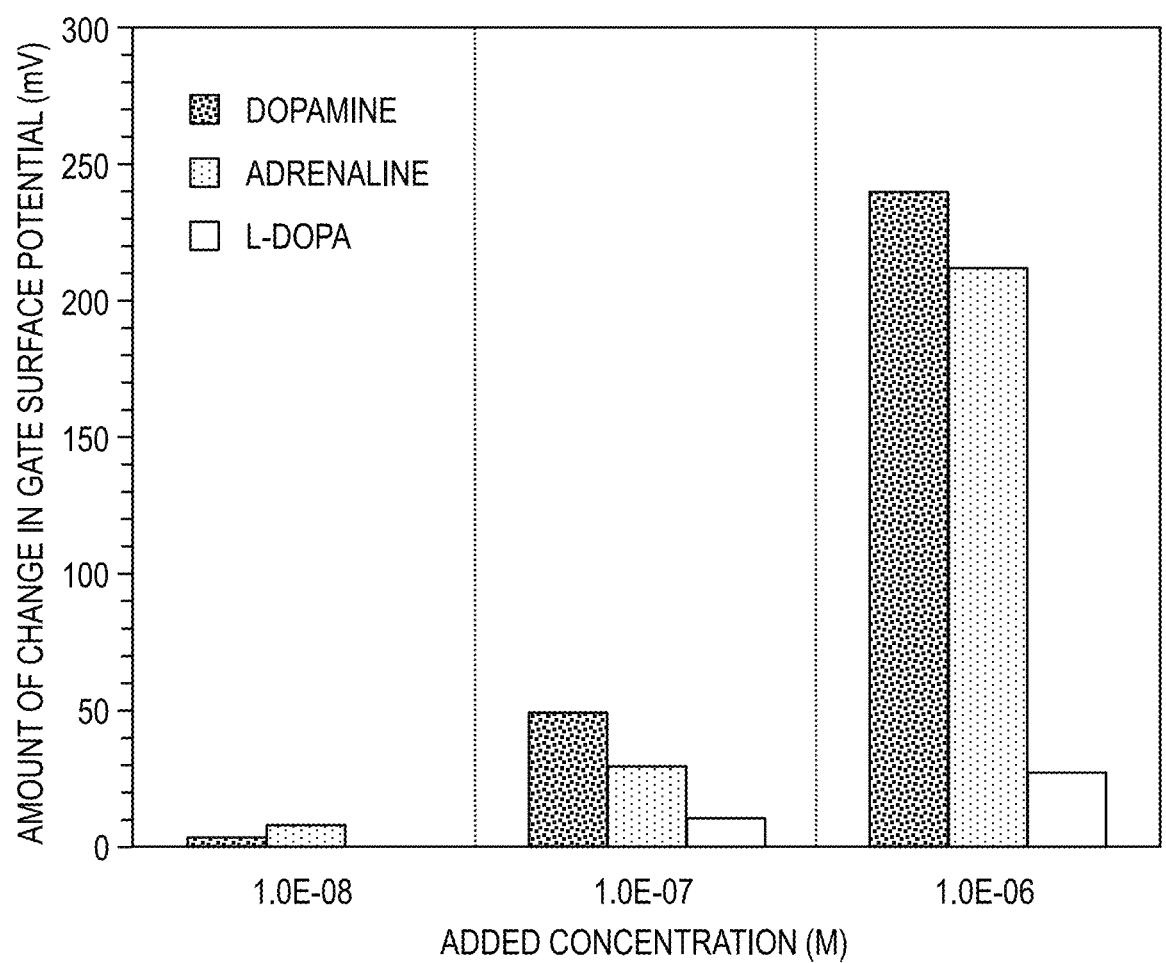

[Figure 9]
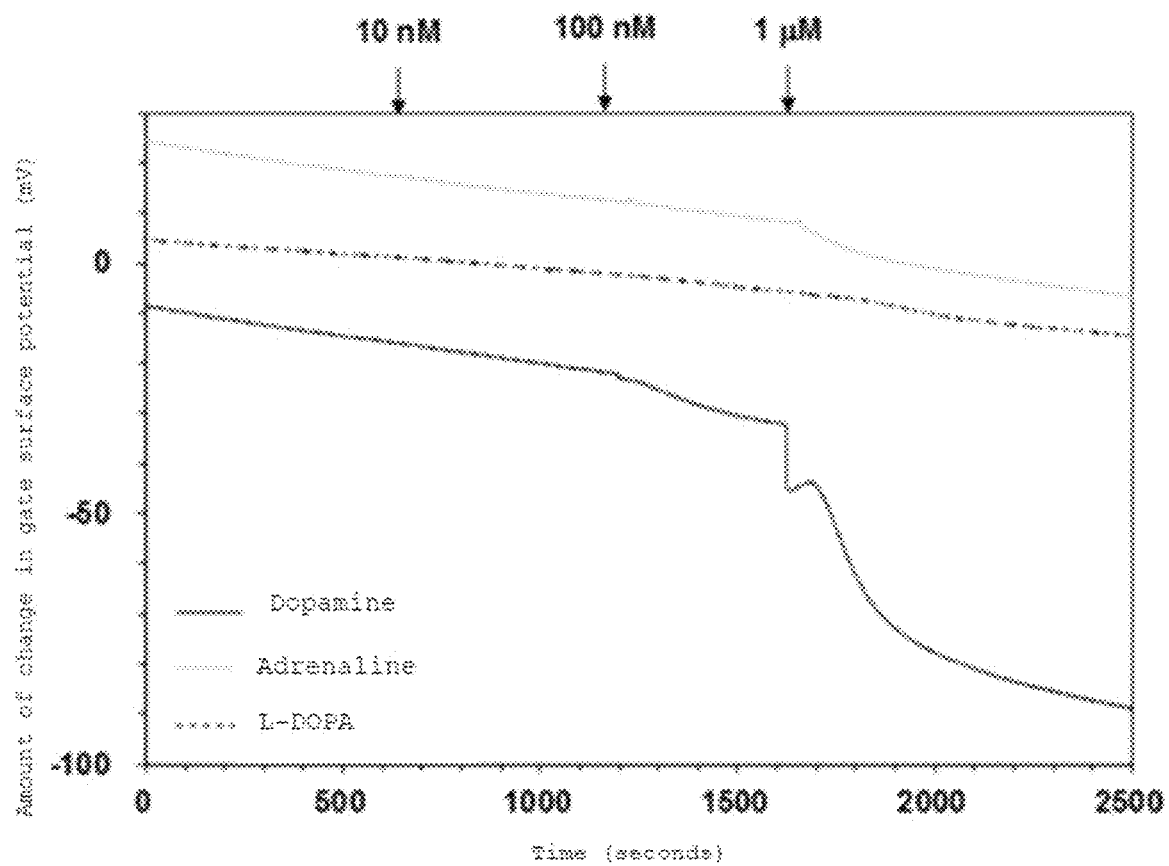

[Figure 10]
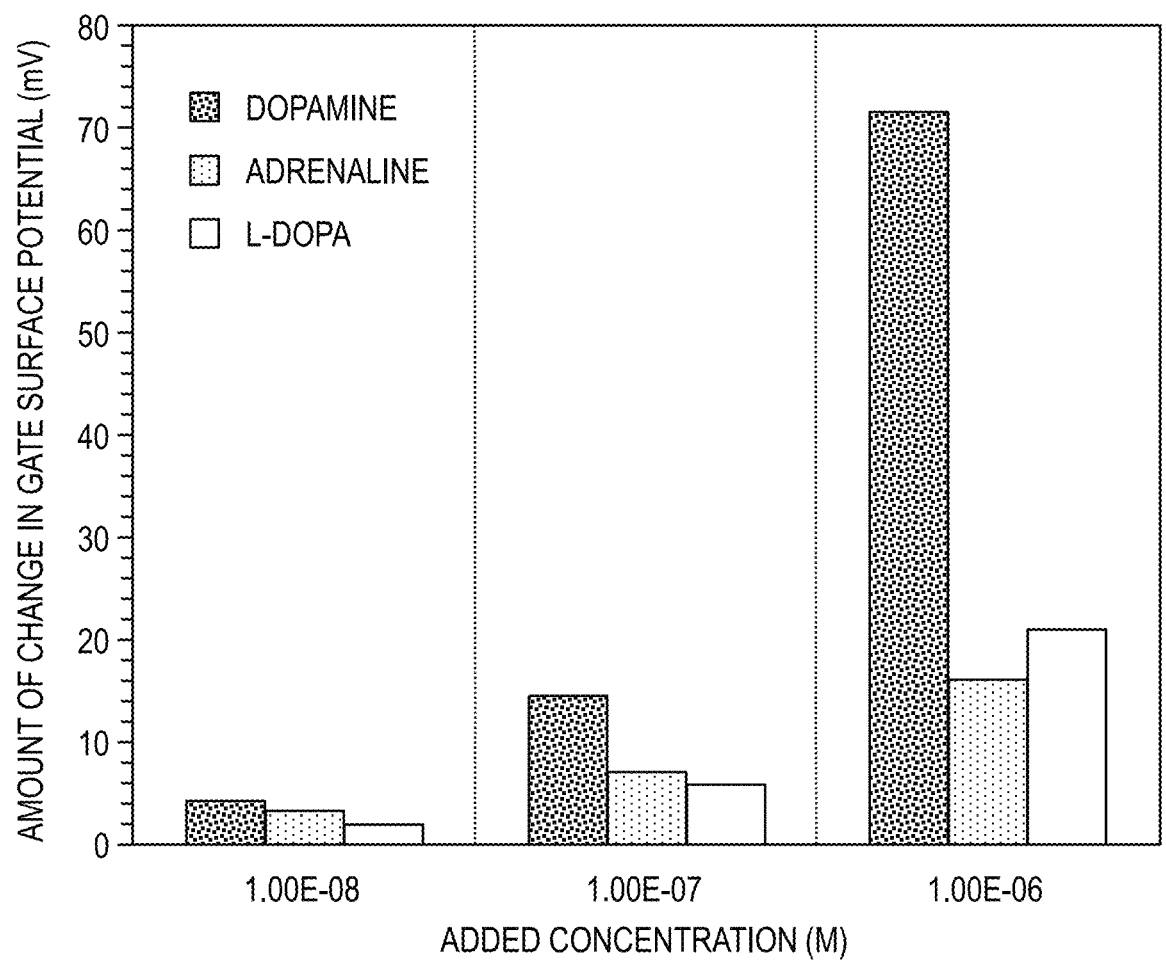

[Figure 11]
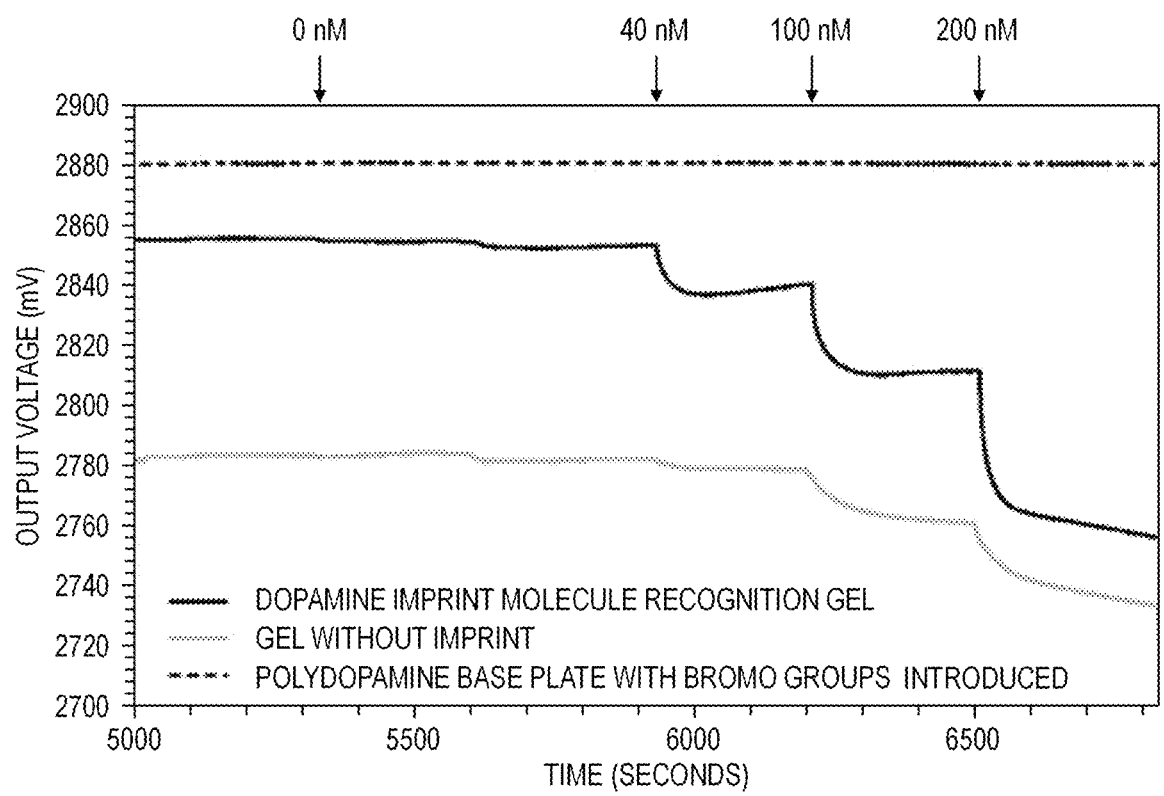

[Figure 12]
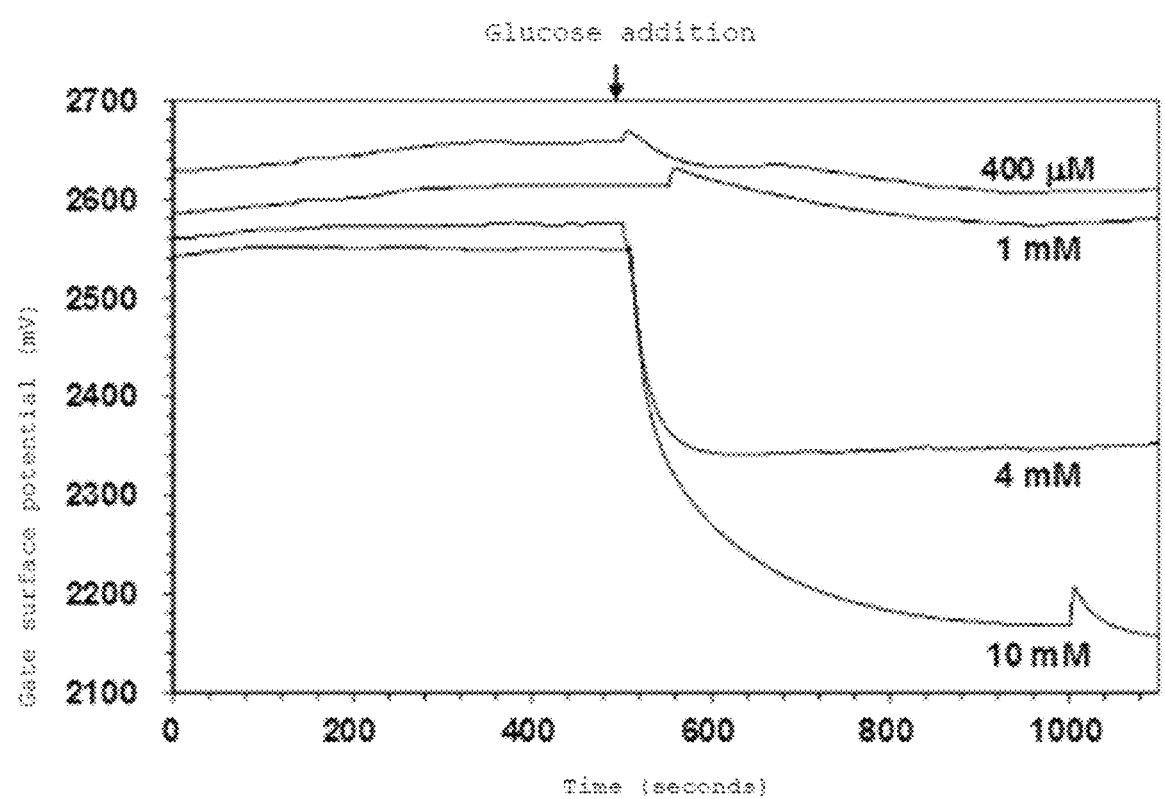

[Figure 13]
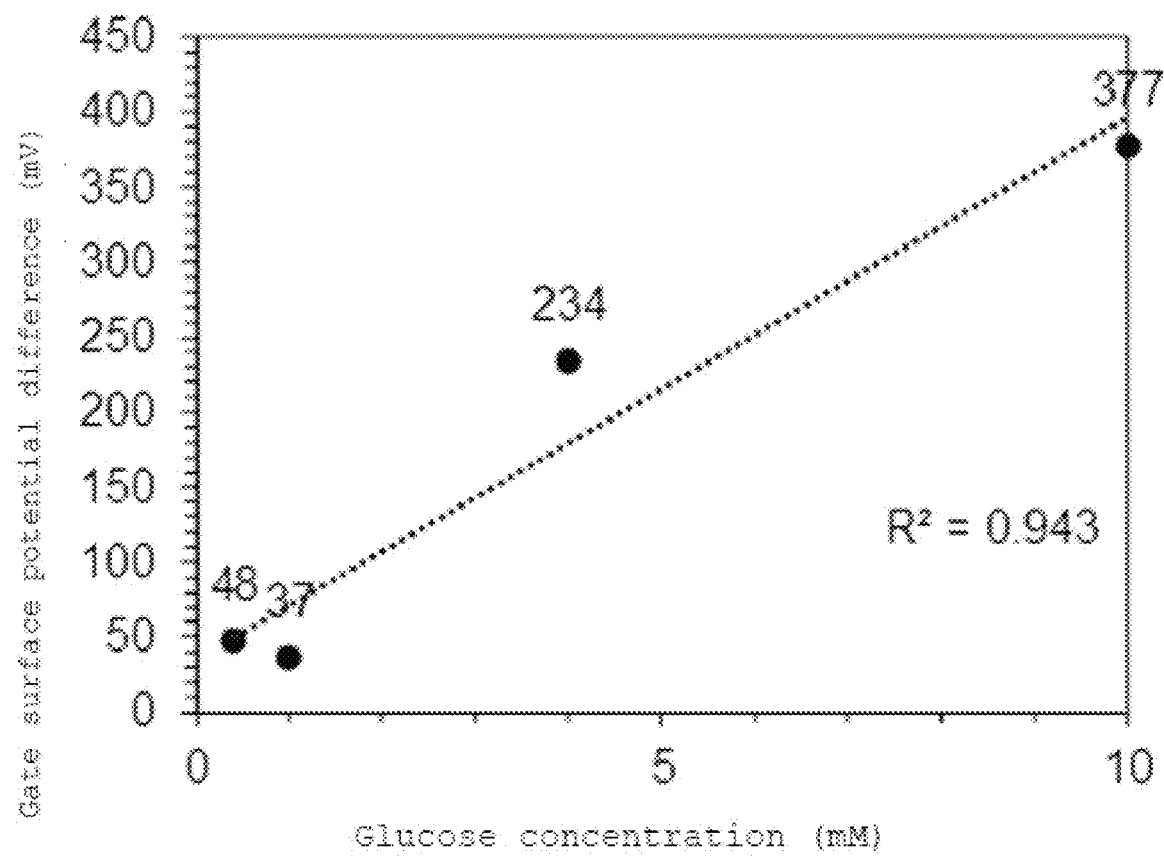

HIGH-SENSITIVITY BIOSENSOR

TECHNICAL FIELD

The present invention relates to a biosensor having superior detection specificity and detection sensitivity.

BACKGROUND ART

In recent years, various biosensors are being researched and developed, as well as being utilized in fields such as medical care, drug discovery, and clinical examination. Biosensors utilize the superior molecular identifying ability of living organisms to recognize information from the outside world (such as chemical factors) as some kind of a physical signal, and various principles and measurement targets exist. In particular, biosensors are a type of chemical sensors that target chemical substances as measurement targets, and are composed of a molecular identifier element that recognizes only the measurement target substance and a signal transformation element that transforms the information acknowledging the recognition into a physical signal such as an electric signal. In general, since biomolecules or compounds that capture biomolecules such as enzymes, antibodies, DNA, cells, and microorganisms are employed for molecular identifier elements, these sensors are called biosensors.

Moreover, although ordinary electronic instruments or chemical sensors such as electrodes, thermistors, crystal oscillators, surface plasmon resonance, and semiconductor elements are used as signal transformation elements, research of biosensors employing field effect transistor (FET) has recently been active. With a biosensor employing FET, when the molecular identifier element recognizes the chemical substance to be the measurement target, physical changes such as heat, mass, and charge as well as chemical changes such as degradation of target substance or generation of the substance occur, these changes are transformed into electric signals with FET which is a signal transformation element as change in charge or change in capacitance, and the target substance is measured. A biosensor employing FET have characteristics such as (1) charges inherent to ions or molecules can be electrically detected, (2) no effort and time is necessary for measurement, (3) real-time measurement is possible, (4) electrical measurement without labeling and without invasion is possible, and (5) downsizing and integration are possible due to semiconductor microproduction technology.

In the past, there has been proposed a highly sensitive biosensor that can be used for trace amounts of non-invasively collected body fluid samples and can measure the target substance with high precision even when trace amounts of sample are employed or when the concentration of the measurement target substance in the sample is low (such as Patent Literature 1).

CITATION LIST

[Patent Literature 1] WO2014/178237

SUMMARY OF THE INVENTION

Problems to be Solved by the Invention

The biosensor according to the above Patent Literature 1 was a groundbreaking invention in that it enabled measurement of trace amounts of measurement target substance contained in body fluids. However, since there are various substances other than the measurement target substance contained in body fluids, in order to put such biosensors into practical use, it was necessary to not only increase the detection sensitivity for the measurement target substance, but to prevent false detection of substances other than the measurement target substance (i.e. increase detection specificity).

Means for Solving the Problems

As a result of repeated extensive investigation by the present inventors to increase the detection specificity of biosensors, it was found that by coating the biosensor gate electrode (the electrode that comes in contact with the test sample) with a catecholamine polymer (polycatecholamine), non-specific adsorption of the substance in the test sample onto said gate electrode is prevented, and detection noise may be almost completely removed.

The present inventors further found that by laminating a layer of molecular imprinted polymer (MIP) on the biosensor gate electrode coated with polycatecholamine, it is possible to create a design so that only the detection target substance in the test sample interacts with the gate electrode. A molecular imprinted polymer as used herein refers to those having a "molecular imprint" having a structure complementary to the molecular structure of the detection target substance formed on said polymer surface or in the polymer by a given production method, and said molecular imprint can have only the said detection target substance integrated.

The present inventors further performed repeated research towards practical use of biosensors having a molecular imprinted polymer applied to a gate electrode. In doing so, the present inventors encountered a new technical problem that although it is true that a biosensor having a molecular imprinted polymer produced by a simplified method applied to a gate electrode has improved specificity against detection target substance compared to conventional technology, detection sensitivity and detection stability against the detection target substance is somewhat reduced due to the thickness of the molecular imprinted polymer layer.

Here, the present inventors have succeeded in controlling the film thickness of the molecular imprinted polymer layer applied to the gate electrode by applying polymer control technology mainly employed in high polymer chemistry field to the present technical field, thereby allowing the molecular imprinted polymer layer to be an ultrathin film layer. Agate electrode having an ultrathin film molecular imprinted polymer layer not only has detection specificity against the detection target substance, but also has extremely high detection sensitivity.

In other words, in one embodiment, the present invention relates to a biosensor characterized in that it comprises an identifier substance that can bind to a detection target substance and an electrode that takes the charge of said identifier substance, wherein the biosensor detects the change in the charge density of said electrode generated by the binding of said detection target substance with said identifier substance, the surface of said electrode is coated with polycatecholamine, all or a part of said electrode surface coated with polycatecholamine further has a polymer layer formed thereon which has a molecular imprint formed therein having a structure complementary to the molecular structure of the detection target substance, said polymer layer comprises said identifier substance, and said polymer layer is an ultrathin film layer.

Moreover, one embodiment of the present invention is characterized in that said polycatecholamine is L-DOPA, dopamine, adrenaline, or noradrenaline polymer.

Moreover, one embodiment of the present invention is characterized in that said ultrathin film layer is a thin film layer having a thickness of 1 µm or less.

Moreover, one embodiment of the present invention is characterized in that said ultrathin film layer is a thin film layer having a thickness of 100 nm or less.

Moreover, one embodiment of the present invention is characterized in that said detection target substance is catecholamine, and said biosensor substantially does not detect L-DOPA.

Moreover, one embodiment of the present invention is characterized in that said detection target substance is dopamine, adrenaline, or noradrenaline.

Moreover, one embodiment of the present invention is characterized in that said identifier substance is phenylboronic acid.

Moreover, one embodiment of the present invention is characterized in that said electrode is a gold electrode, a silver electrode, a copper electrode, a platinum electrode, an indium-tin oxide (ITO) electrode, a palladium electrode, a steel electrode, a nickel titanium alloy electrode, a titanium oxide electrode, a silicon dioxide electrode, a crystal electrode, an aluminum oxide electrode, a gallium arsenide electrode, a glass electrode, or a tantalum oxide electrode.

Moreover, one embodiment of the present invention is characterized in that said electrode is electrically connected to the gate electrode of a field effect transistor.

Moreover, one embodiment of the present invention is characterized in that said electrode is placed away from said field effect transistor, and said electrode is electrically connected to said gate electrode of said field effect transistor via electric wiring.

Moreover, one embodiment of the present invention is characterized in that said electrode is electrically connected to said gate insulator film by being directly mounted on the gate insulator film of said field effect transistor.

Moreover, one embodiment of the present invention is characterized in that said electrode is electrically connected to a signal amplifier.

Moreover, one embodiment of the present invention is characterized in that said signal amplifier is an operational amplifier.

Moreover, one embodiment of the present invention is characterized in that said polymer layer is formed by a method comprising:

(a): a step of polymerizing a monomer solution comprising one or more types of monomers, said detection target substance, and said identifier substance on all or a part of the surface of said electrode to allow formation of a polymer layer which is an ultrathin film layer on all or a part of the surface of said electrode, and (b): after said step (a), a step of removing said detection target substance from said polymer layer to allow formation of a molecular imprint having a structure complementary to the molecular structure of said detection target substance on said polymer layer.

Moreover, one embodiment of the present invention is characterized in that the polymerization of said monomer solution is living radical polymerization or electrolytic polymerization.

Moreover, one embodiment of the present invention is characterized in that said living radical polymerization is atom transfer radical polymerization (ATRP), reversible addition/fragmentation chain transfer polymerization (RAFT), or nitroxide-mediated polymerization (NMP).

Moreover, one embodiment of the present invention is characterized in that said living radical polymerization is atom transfer radical polymerization (ATRP), and prior to said step (a), polymerization initiator molecules are bound in advance to all or a part of the electrode surface.

Moreover, one embodiment of the present invention is characterized in that said step (a) is a step of applying a monomer solution comprising one or more types of monomers, said detection target substance, and said identifier substance to all or a part of the electrode surface with a spin coat, and polymerizing the applied monomer solution to allow formation of an ultrathin film polymer layer on all or a part of the surface of said electrode.

Moreover, one embodiment of the present invention is characterized in that said monomer solution comprises at least one monomer selected from the group consisting of acrylamide derivative, methacrylamide derivative, acrylate derivative, methacrylate derivative, acrylonitrile, 2-vinylpyridine, 4-vinylpyridine, N-vinyl-2-pyrrolidone, and vinyl acetate.

Moreover, another embodiment of the present invention relates to an electrode used in a biosensor, characterized in that said biosensor is a biosensor that detects the change in the charge density of said electrode generated by the binding of the detection target substance with the identifier substance, said electrode is an electrode that takes the charge of said identifier substance that can bind to said detection target substance, the surface of said electrode is coated with polycatecholamine, all or a part of the surface of said electrode coated with polycatecholamine further has a polymer layer formed thereon which has a molecular imprint formed therein having a structure complementary to the molecular structure of the detection target substance, said polymer layer comprises said identifier substance, and said polymer layer is an ultrathin film layer.

Note that an invention of any combination of one or more characteristics of the present invention described above is also encompassed by the scope of the present invention.

BRIEF DESCRIPTION OF THE DRAWINGS

FIG. 1 shows a schematic diagram showing the outline configuration of the ion-sensitive biosensor employed in Example 1.

FIG. 2 shows a graph showing the change in the gate surface potential of FET when a substance not targeted for detection (dopamine) was added to the electrode of the ion-sensitive biosensor employed in Example 1.

FIG. 3 shows a graph showing the change in the gate surface potential of FET when a substance not targeted for detection (albumin) was added to the electrode of the ion-sensitive biosensor employed in Example 1.

FIG. 4 shows a schematic diagram showing the outline configuration of the biosensor according to one embodiment of the present invention.

FIG. 5 shows a graph showing the change in the gate surface potential of FET, which shows the effect of suppressing the adsorption of catecholamines molecules onto a gold electrode by a polydopamine thin film layer.

FIG. 6 shows a graph showing the change in the gate surface potential of FET, which shows the adsorption of catecholamines molecules onto a gold electrode.

FIG. 7 shows a graph showing the change in the gate surface potential of FET when each substance was added to an extended FET having formed a polydopamine thin film layer and a molecular imprinted polymer layer against dopamine on a gold electrode.

FIG. 8 shows a bar graph showing the amount of change in the gate surface potential of FET when each substance at various concentrations was added to an extended FET having formed a polydopamine thin film layer and a molecular imprinted polymer layer against dopamine on a gold electrode.

FIG. 9 shows a graph showing the change in the gate surface potential of FET when each substance was added to an extended FET having formed a polydopamine thin film layer and a molecular imprinted polymer layer against dopamine on a gold electrode.

FIG. 10 shows a bar graph showing the amount of change in the gate surface potential of FET when each substance at various concentrations was added to an extended FET having formed a polydopamine thin film layer and a molecular imprinted polymer layer against dopamine on a gold electrode.

FIG. 11 shows a graph showing the change in the gate surface potential of FET when dopamine was added to an extended FET having formed a polydopamine thin film layer and a molecular imprinted polymer layer against dopamine on a gold electrode.

FIG. 12 shows a graph showing the change in the gate surface potential of FET when glucose was added to an extended FET having formed a poly L-DOPA thin film layer and a molecular imprinted polymer layer against glucose on a gold electrode.

FIG. 13 is a figure of plotting experimental result shown in FIG. 12 by the two axes of the change in the gate surface potential and glucose concentration.

DESCRIPTION OF EMBODIMENTS the biosensor of the present invention is based on a basic principle to detect the electric change generated by the binding between a detection target substance and an identifier substance that can specifically or selectively bind to the said detection target substance as the change in electrode charge density (details will be described below). The "detection target substance" as used herein is not limited as long as a molecular imprinted polymer corresponding to the said substance can be manufactured, and those skilled in the art can set various substances as detection targets based on technical common sense.

Employment of the biosensor of the present invention can be utilized for detecting trace amounts of substances in various test samples, for example, the biosensor of the present invention can be employed to detect biologically derived substances, substances in the environment, or substances in food. In particular, since the present invention allows detection even when the concentration of the detection target substance in the test sample is extremely low, it can be favorably utilized for e.g. detection of substances in body fluids (blood, lymph, tissue fluid, body cavity fluid, digestive juice, sweat, tear, nasal discharge, saliva, urine, seminal fluid, vaginal fluid, amniotic fluid, lactation, and the like). Examples of substances in the body fluid include, for example, body fluid components (e.g. alkaline phosphatase, AST, ALT, lactate dehydrogenase, leucine aminopeptidase, γ-GTP, creatine kinase, cholinesterase, bilirubin, bile acid, albumin, urea nitrogen, creatinine, uric acid, HDL cholesterol, LDL cholesterol, neutral fat, glucose, amylase, lipase, sodium, potassium, chloride, calcium, inorganic phosphorus, magnesium, zinc, iron, ferritin, C-reactive protein, β2-microglobulin, hemoglobin A1C, glycoalbumin, ammonia, various hormone, various neurotransmitters (e.g. monoamines such as catecholamine, serotonin, melatonin, and histamine; amino acids such as aspartic acid, glutamic acid, γ-aminobutyric acid, glycine, and taurine; acetylcholine; nerve peptides), and the like, which are components that are subject to inspection in general blood biochemical tests), disease-related biomarkers (for example, tumor markers, autoimmune disease markers, central nervous system disease markers, cardiac disease biomarkers, and the like), pathogens (e.g. virus, bacteria, fungus, parasite, and the like) as well as their related factors, and drug molecules of previously administered agents.

The "identifier substance that can bind to a detection target substance" as used herein can be appropriately selected by those skilled in the art depending on the detection target substance. The said identifier substance may be a substance that specifically binds to the detection target substance, or may be a substance that selectively binds to the detection target substance.

Examples of the "identifier substance that can bind to a detection target substance" as used herein can include, for example, either member of the pairs of substances known to generate specific or selective interaction (e.g. glucose and phenylboronic acid, lactic acid and phenylboronic acid, histamine and carboxyl group monomer, uric acid and carboxyl group monomer, creatinine and carboxyl group monomer, sialic acid and phenylboronic acid & amino group monomer, dopamine and phenylboronic acid & amino group monomer, biotin and streptavidin), aptamers that specifically bind to particular molecules (e.g. nucleic acid aptamer, peptide aptamer), either member of the receptor-ligand (or agonist) combination, antibodies that specifically bind to the detection target substance (e.g. a monoclonal antibody that specifically binds to the detection target substance) or an antigen binding fragment thereof, and nucleic acids that specifically bind to the detection target substance (e.g. a nucleic acid having a sequence complementary to the nucleic acid of interest).

In the present invention, the method for allowing the formation of a molecular imprint having a structure complementary to the molecular structure of the detection target substance onto a polymer layer is not limited, and various methods known to those skilled in the art as methods for forming a molecular imprinted polymer can be employed. Specifically, a molecular imprinted polymer can be produced by polymerizing a monomer solution comprising the detection target substance to obtain a polymer, and then removing the detection target substance from the said polymer.

In the present invention, the monomer solution for producing the molecular imprinted polymer comprises one or two or more monomers. Examples of monomers contained in the monomer solution include, for example, one or more monomers selected from the group consisting of acrylamide derivatives (such as acrylamide, dimethyl acrylamide, N-isopropyl acrylamide, N-methylol acrylamide, and acryloyl morpholine), methacrylamide derivatives (such as methacrylamide, dimethyl methacrylamide, N-isopropyl methacrylamide, N-methylol methacrylamide, and methacryloyl morpholine), acrylate derivatives (hydroxyethyl acrylate, hydroxypropyl acrylate, dimethylaminoethyl acrylate, and dimethylaminopropyl acrylate), methacrylate derivatives (such as hydroxyethyl methacrylate, hydroxypropyl methacrylate, dimethylaminoethyl methacrylate, and dimethylaminopropyl methacrylate), acrylonitrile, 2-vinylpyridine, 4-vinylpyridine, N-vinyl pyrrolidone, or vinyl acetate.

In the present invention, the method for removing the detection target substance from the polymer comprising the detection target substance is not limited, and can be appropriately selected by those skilled in the art depending on the type of the detection target substance and the type of the monomer employed. Examples that the combination of detection target substance-identifier substance-removal method is not limited and can include the following.

glucose-phenylboronic acid-hydrochloric acid/methanol
lactic acid-phenylboronic acid-hydrochloric acid/methanol
histamine-carboxyl group monomer-acetic acid/methanol/acetonitrile
uric acid-carboxyl group monomer-acetic acid/methanol/acetonitrile
creatinine-carboxyl group monomer-acetic acid/methanol/acetonitrile
sialic acid-phenylboronic acid & amino group monomer-hydrochloric acid/methanol
dopamine-phenylboronic acid & amino group monomer-hydrochloric acid/methanol The biosensor of the present invention is characterized in that the molecular imprinted polymer layer applied to the electrode surface is an ultrathin film layer. The method for controlling the thickness of the polymer layer is not limited, and various methods well-known in the high polymer chemistry field may be employed. For example, a method for controlling the thickness of the polymer layer with a chemical method or a method for producing a thin polymer layer with a physical method can be employed as methods for controlling the thickness of the polymer layer.

As chemical methods for controlling the thickness of the polymer layer that can be employed in the present invention, for example living radical polymerization or electrolytic polymerization can be employed. In particular, since the thickness of the polymer layer can be controlled by polymerization time in living radical polymerization, it can be favorably employed for production of a uniform polymer layer with nano-order thickness.

Nitroxide-Mediated Polymerization (NMP; e.g. Japanese Published Unexamined Patent Application Publication No. S60-89452), Atom Transfer Radical Polymerization (ATRP; e.g. Japanese Translation of PCT International Application Publication No. H10-509475), and Reversible Addition/Fragmentation Chain Transfer Polymerization (RAFT; e.g. International Publication No. 98/01478) are known as living radical polymerization methods. In the present invention, an appropriate method from any of these polymerization methods can be selected and employed depending on the nature of the detection target substance or the required detection procedure.

Moreover, Activator ReGenerated by Electron Transfer (ARGET) ATRP method has been reported, in which a reductant is added to reduce the bivalent copper produced in the ATRP system into continuously active monovalent copper with the purposes of improving the polymerization speed, convenience of manipulation, and the like (e.g. Angew Chem, Int Ed, 45(27), 4482 (2006)). Since the thickness of the polymer layer can be controlled without requiring strict vacuum state with this method, it can also be favorably employed in the present invention.

Polymerization can be performed without any solvent or in various solvents. Preferred solvents can include anisole, toluene, ethylbenzene, tetrahydrofuran, dimethylformamide, dimethyl sulfoxide, and the like.

The amount of the polymerization solvent used is not particularly limited, and is preferably within the range of 0-2000 parts by mass, and more preferably within the range of 10-1000 parts by mass to 100 parts by mass of the monomer. The upper limit values of each of these ranges has significance in suppressing the decline in polymerization speed and controlling polymerization.

A compound having a group commonly known to be a polymerization initiator molecule of living radical polymerization can be favorably used as the polymerization initiator molecule. For example, organic alkyl halides, organic peroxides, azo-based compounds, inorganic peroxides, redox type polymerization initiators, and the like can be employed.

It is preferred that a catalyst is used for polymerization. The type of catalyst can be appropriately selected depending on the polymerization method from among various commonly known catalysts. For example, when ATRP is employed as the polymerization method, a metal catalyst comprising metals such as Cu(0), Cu+, Cu2+, Fe+, Fe2+, Fe3+, Ru2+, and Ru3+ can be used. In order to achieve high level of control over molecular weight or molecular weight distribution, monovalent copper compounds comprising Cu+ or 0-valent copper are particularly preferred. Specific examples thereof include Cu(0), CuCl, CuBr, Cu2O, and the like.

Moreover, organic ligands are ordinarily used for the metal catalysts described above. Ligand atoms to metals include e.g. nitrogen atoms, oxygen atoms, phosphorus atoms, sulfur atoms, and the like. Among these, nitrogen and phosphorus atoms are preferred. Specific examples of organic ligands include 2,2'-bipyridine and derivatives thereof, 1,10-phenanthroline and derivatives thereof, tetramethylethylenediamine, pentamethyldiethylenetriamine, Tris (dimethylaminoethyl)amine (Me6TREN), triphenylphosphine, tributylphosphine, and the like.

An example of the physical method for controlling the thickness of the polymer layer that can be employed in the present invention includes a method employing a spin coat. Specifically, a monomer solution is applied to the surface to be the target, unnecessary monomer solution is removed by high-speed spinning with a spin coat device, and then this is polymerized to produce a polymer layer with nano-order thickness. Moreover, the thickness of the polymer layer by this method can be adjusted by the spinning speed of the spin coat device.

With respect to increasing detection sensitivity, the thickness of the molecular imprinted polymer layer employed in the biosensor of the present invention is preferably 1 µm or less, and more preferably 100 nm or less. The preferred upper and lower limits of the thickness of the molecular imprinted polymer layer employed in the biosensor of the present invention will vary depending on the detection target substance, and may be e.g. 1 µm, 500 nm, 400 nm, 300 nm, 200 nm, 100 nm, or 50 nm for the upper limit and 1 nm, 3 nm, 5 nm, 8 nm, 10 nm, 15 nm, 20 nm, or 30 nm for the lower limit. For example, the thickness of the polymer layer may be 1 nm-1 µm, may be preferably 3 nm-500 nm, may be further preferably 5 nm-100 nm, and may be most preferably 5 nm-50 nm. Understandably, the thickness of the molecular imprinted polymer layer employed in the biosensor of the present invention does not need to have strictly uniform thickness in all of its area, and may only need to be within the above range of thickness in average.

In the present invention, the method for measuring the thickness of the molecular imprinted polymer layer is not particularly limited, and measurement can be performed with any method well-known in the art. For example, the thickness of the molecular imprinted polymer layer can be measured with an atomic force microscope (AFM) or a commercially available ellipsometer.

The biosensor of the present invention is characterized in that measurement noise arising from non-specific adsorption of contaminants (e.g. proteins such as albumin) in the test sample to the electrode is considerably reduced due to all or a part of the electrode surface that comes in contact with the test sample being coated with polycatecholamine. "Catecholamine" herein is a generic term for compounds that are induced from tyrosine and possesses a catechol and an amine, examples of which L-DOPA, dopamine, noradrenaline, adrenaline, and the like are known. Moreover, "polycatecholamine" means a catecholamine polymer, examples of which include L-DOPA, dopamine, noradrenaline, and adrenaline polymer.

The method for coating polycatecholamine onto the electrode surface is not particularly limited, and can be appropriately selected by those skilled in the art. For example, since catecholamine is polymerized by oxidation, polymerization by auto-oxidation (air oxidation) can be induced by applying a catecholamine solution onto the electrode surface and letting it stand still. Other oxidation methods include, e.g. electrochemical oxidation (such as cyclic voltammetry), UV ozone oxidation, addition of an oxidant such as potassium permanganate, and the like.

[Configuration of the Biosensor]

An example of the biosensor according to one embodiment of the present invention will be shown, and the configuration thereof will be described. FIG. 4 is a schematic diagram showing the outline configuration of biosensor 200 which is one embodiment of the present invention. Note that in the description below, description is made by way of an example when dopamine is used as the detection target substance and a so-called extended-gate FET is used as the detection element, but the biosensor according to the present invention is not to be limited to such an example. For example, an ordinary FET where the gate electrode is directly mounted on the insulator film may be employed.

Moreover, the biosensor according to the present invention is not limited to those employing FET as the detection element. The essential characteristic of the present invention is to detect the presence of the detection target substance in the test sample as an electric signal in the electrode portion coated with polycatecholamine, and for example, the said electrode connected to a signal amplifier (such as a vacuum tube, a transistor, an operational amplifier, or a magnetic amplifier) can also be used as a biosensor.

As shown in FIG. 4, biosensor 200 according to one embodiment of the present invention is a biosensor that employs FET device 201 as the detection element for detecting the detection target substance (dopamine), and mainly comprises a molecular identifier component (in FIG. 4, extended-gate electrode 206, polycatecholamine thin film layer 207, and molecular imprinted polymer layer 208 will be collectively called the "molecular identifier component") and FET device 201. Extended-gate electrode 206 is sputtered onto base plate 205, polycatecholamine thin film layer 207 is coated on extended-gate electrode 206, and molecular imprinted polymer layer 208 is further provided on the polycatecholamine thin film layer 207. Moreover, extended-gate electrode 206 is electrically connected to the gate electrode 203 on the oxide gate insulator 202 via electric wiring 204. The molecular identifier component is connected to the FET device 201 via the oxide gate insulator 202, and serves also as the gate electrode in FET. Here, molecular imprinted polymer layer 208 comprises phenylboronic acid, and a molecular imprint having a structure complementary to the molecular structure of dopamine is formed on the surface and interior thereof.

Moreover, on base plate 205 is fixed a glass ring so as to surround the molecular identifier component, and buffer 210 is filled inside the glass ring.

Note that as shown in FIG. 4, reference electrode 209 may be provided as necessary. Reference electrode 209 is provided in buffer 210, and forms a closed circuit together with the source and drain electrodes of the FET device 201. Reference electrode 209 is the electrode to be the reference potential for voltage measurement in FET, and may sometimes be grounded. In practice, although it will be necessary for voltage measurement in FET, reference electrode 209 does not need to be provided if it can be substituted with another well-known method.

The semiconductor base plate of the FET device 201 is for example a p-type semiconductor, and a part thereof (such as two places) is locally doped to form a n-type semiconductor portion on which the source and drain electrodes are provided. In other words, the FET used in glucose sensor 100 is a so-called n-channel MOSFET (Metal Oxide Semiconductor Field Effect Transistor). Note that the FET used in the biosensor according to the present invention is not limited to the above n-channel MOSFET (n-MOS), and may be p-channel MOSFET (p-MOS), n-channel junction FET, or p-channel junction FET.

Moreover, the material for the semiconductor base plate is not particularly restricted, and well-known semiconductors such as Si, GaAs, transparent oxide semiconductors (such as ITO, IGZO, and IZO), organic semiconductors, and carbon semiconductors (such as carbon nanotube, graphene semiconductor, and diamond semiconductor etc.) can be appropriately selected and employed. Note that when carbon semiconductors are employed as the material for the semiconductor base plate, the measurement sensitivity of biosensor 200 may be elevated compared to when Si is used (may be measured with high precision even when the detection target substance in the test sample concentration is low).

The measurement principle of biosensor 200 according to one embodiment of the present invention shown in FIG. 4 will be described next. When the test sample is added to the buffer 210, only the dopamine molecules in the test sample are integrated into the molecular imprint formed on the surface and interior of the molecular imprinted polymer layer 208. Since the molecular imprinted polymer layer 208 comprises phenylboronic acid that specifically reacts to dopamine, glucose that penetrated into the molecular imprinted polymer layer 208 reacts to the said phenylboronic acid. At least either one of charge density and capacitance in the molecular identifier component changes due to the reaction between the phenylboronic acid in the molecular imprinted polymer layer 208 and glucose, and FET detects this as the change in potential to allow measurement of the presence or concentration of the detection target substance.

Note that if there exists even a part of the extended-gate electrode 206 that is not covered by the molecular imprinted polymer 208, substances (e.g. proteins such as albumin) in the test sample are non-specifically adsorbed onto the extended-gate electrode 206, and measurement noise may be generated. However, in the present invention, since the extended-gate electrode 206 is covered with the polycatecholamine thin film layer 207, even if there existed a place in a part of the extended-gate electrode 206 that is not covered by the molecular imprinted polymer 208, measurement noise due to non-specific adsorption will not be generated.

Moreover, biosensor 200 uses the extended-gate FET as described above as the detection element. With a biosensor employing extended-gate FET 200, the molecular identifier component is separated from the FET main body (FET device 201 comprising a semiconductor base plate having source and drain electrodes provided thereon), and the molecular identifier component can be freely detached and connected to the FET device 201.

In other words, it is possible to separately prepare the molecular identifier component and the FET device, and then them use in combination. As disclosed in the specification of the present invention, since the molecular identifier component can be altered to specifically detect various detection target substances, for example, by configuring the molecular identifier components corresponding to the various detection target substances as detachable chips to the detection device main body (FET device), detection of diverse factors will be possible with one detection device.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, shall not be construed as being limited to the Examples described herein.

EXAMPLES

Example 1: Noise Removal Effect by Coating of Polycatecholamine onto the Electrode In order to show the noise removal effect by coating the electrode with various polycatecholamines (L-DOPA, dopamine, adrenaline, or noradrenaline polymer), an ion-sensitive biosensor having a polydopamine thin film layer laminated onto a gold electrode was first produced.

(1) Production of Ion-Sensitive Biosensor Having Polycatecholamine Thin Film Layer Laminated onto Gold Electrode The ion-sensitive sensor employed in the present Example was produced as follows (schematic diagram of the configuration is shown in FIG. 1).

In the ion-sensitive sensor employed in the present Example, MOSFET (from NXP, 2N7002) was employed as the detection element. As the electrode (ion-sensitive electrode) for detecting the charge of the target subject, a 6 mm diameter gold electrode sputtered onto a glass base plate was employed to produce a polycatecholamine thin film layer on the gold electrode by the method described below. Said gold electrode was set as an extended-gate electrode by electric connection via electric wiring from the gate electrode which is in direct contact with said MOSFET.

Next, in the present Example, in order to perform measurement in a solution, a glass ring having an outer diameter or 12 mm, an inner diameter of 10 mm, and a height of 10 mm was fixed onto the ion-sensitive electrode obtained as described above (the gold electrode coated with a polycatecholamine thin film layer) with epoxy resin.

(2) Production of Polycatecholamine Thin Film Layer onto Gold Electrode

L-DOPA powder (D0600, Tokyo Chemical Industry Co., Ltd.), dopamine powder (A0305, Tokyo Chemical Industry Co., Ltd.), noradrenaline powder (A0906, Tokyo Chemical Industry Co., Ltd.), or adrenaline powder (A0173, Tokyo Chemical Industry Co., Ltd.) were each dissolved in Tris buffer (100 mM, pH 10) to produce 25 mM catecholamine solutions (L-DOPA solution, dopamine solution, noradrenaline solution, or noradrenaline solution). Next, 500 µl of one of the catecholamine solutions was placed in the above gold electrode having a glass ring fixed thereon, a polycatecholamine thin film layer was formed on the gold electrode by irradiating UV for 5 minutes with an ultraviolet ray ozone surface treatment/reforming device (from MIZUKA PLANNING, PL-16) and then leaving at room temperature for 24 hours.

As a Comparative Example, an ion-sensitive biosensor having a gold electrode (i.e. a gold electrode without coating with polycatecholamine) which has undergone a procedure similar to the above except that a simple Tris buffer (100 mM, pH10) was applied to the gold electrode having a glass ring fixed thereon was prepared.

(3) Noise Removal Effect by Polycatecholamine Thin Film Layer

A comparative experiment in order to show that the ion-sensitive sensor according to the present Example considerably reduces noise due to non-specific adsorption compared to the ion-sensitive sensor of the Comparative Example was performed.

(3-1) Comparative Experiment Employing Dopamine as Example of Contaminant

Five hundred microliters of sodium phosphate buffer (Phosphate buffered saline, PBS, pH 7.4) was placed in the glass ring of the ion-sensitive sensor according to the present Example, and dopamine was added so that the final concentration will be 100 nM and 10 µm after gate potential stabilization. Moreover, a similar test was performed with the ion-sensitive sensor according to the Comparative Example.

Note that the "dopamine" added to PBS in the present Example was employed as an example of a contaminant (i.e. a substance that causes non-specific adsorption to the electrode) other than the detection target (hydrogen ion).

The result of the comparative experiment is shown in FIG. 2. The vertical axis in FIG. 2 shows the change in surface potential (mV) of polycatecholamine, and the horizontal axis shows the measurement time (seconds).

As shown in FIG. 2, the ion-sensitive sensor according to the present Example hardly showed any reaction to addition of dopamine (i.e. a substance not targeted for detection) in terms of the gate surface potential. On the other hand, the ion-sensitive sensor having a gold electrode without coating with polycatecholamine (Comparative Example) reacted to addition of dopamine and a negative potential shift was recognized.

(3-2) Comparative Experiment Employing Albumin as Example of Contaminant

Five hundred microliters of sodium phosphate buffer (Phosphate buffered saline, PBS, pH 7.4) was placed in the glass ring of the ion-sensitive sensor according to the present Example, and albumin was added so that the final concentration will be 1 g/L and 5 g/L after gate potential stabilization. Moreover, a similar test was performed with the ion-sensitive sensor according to the Comparative Example.

Note that the "albumin" added to PBS in the present experiment was employed as an example of a contaminant (i.e. a substance that causes non-specific adsorption to the electrode) other than the detection target (hydrogen ion).

The result of the comparative experiment is shown in FIG. 3. The vertical axis in FIG. 3 shows the change in surface potential (mV) of polycatecholamine, and the horizontal axis shows the measurement time (seconds).

As shown in FIG. 3, with the ion-sensitive sensor of the present invention, hardly showed any reaction to addition of albumin (i.e. a substance not targeted for detection) in terms of the gate surface potential. On the other hand, with the ion-sensitive sensor having a gold electrode without coating with polycatecholamine (Comparative Example), and a negative potential shift in reaction to addition of albumin was recognized.

From the above results, it was shown that noise due to adsorption of substances not targeted for detection to the biosensor electrode can be almost completely eliminated by coating the electrode with various polycatecholamines (L-DOPA, dopamine, adrenaline, or noradrenaline polymer).

Example 2: Production of Biosensor that Specifically Detects Detection Target Substance Utilizing the electrode coated with polycatecholamine shown in Example 1, a biosensor that specifically detects the detection target substance which is one embodiment of the present invention was produced. In the present Example, an example employing "dopamine" as the detection target substance is shown.

(1) Designing of Catecholamine Sensor

The catecholamine sensor which is one embodiment of the present invention employed in the present Example was produced as described below (schematic diagram of the configuration is shown in FIG. 4).

In the biosensor employed in the present Example, MOSFET (from NXP, 2N7002) was employed as the detection element. As the electrode for detecting the charge of the target subject, a 6 mm diameter gold electrode sputtered onto a glass base plate was employed to produce a polydopamine thin film layer as well as an ultrathin film polymer layer having formed therein a molecular imprint having a structure complementary to the molecular structure of catecholamine on the gold electrode by the method described below. Said gold electrode (the electrode for detecting the charge of the target subject) was set as an extended-gate electrode by electric connection via electric wiring from the metal electrode (gate electrode) which is in direct contact with said MOSFET.

Said polymer layer comprises as a component thereof a substance (phenylboronic acid) that specifically binds to catecholamine, and when catecholamine fits in the molecular imprint formed on the polymer layer, the said catecholamine binds to the phenylboronic acid in the polymer layer. The catecholamine sensor which is one embodiment of the present invention determines the presence of catecholamine in the target subject by detecting the change in electrode charge density generated by the said binding.

In the present Example, for convenience, said electrode for detecting the charge of the target subject and said polymer layer are inclusively referred to as a "molecular identifier component".

Next, in the present Example, in order to perform measurement in a solution, a glass ring having an outer diameter or 12 mm, an inner diameter of 10 mm, and a height of 10 mm was fixed onto the molecular identifier component obtained as described above with epoxy resin.

(2) Formation of Polydopamine Thin Film Layer that Inhibits Adsorption of Substance not Targeted for Detection to Gold Electrode Dopamine powder (A0305: From Tokyo Chemical Industry Co., Ltd.) was dissolved in phosphate buffer (Phosphate buffered saline, PBS, pH 7.4) to produce a 5 mg/ml dopamine solution, and this was degassed by 10 minutes of nitrogen bubbling. Next, 500 µl of the dopamine solution was placed in the above gold electrode having a glass ring fixed thereon, and a polydopamine thin film layer was formed on the gold electrode by irradiating UV for 1 minute with an ultraviolet ray ozone surface treatment/reforming device (from MIZUKA PLANNING, PL-16).

As a Comparative Example, a gold electrode produced with a method similar to the above except that PBS buffer only was used instead of the dopamine solution (i.e. a gold electrode without coating with polydopamine) was prepared.

(3): Verification of Effect of Polydopamine Thin Film Layer

Experiments were carried out with the gold electrode comprising the polydopamine thin film layer produced in (2) and the gold electrode without a polydopamine thin film layer (Comparative Example).

First, 500 µl of PBS buffer was added to the above gold electrode portion. Keeping the gate potential at 0 V and the source-drain electric current constant at 90 µA with a FET real-time measuring device, adrenaline (A0173, Tokyo Chemical Industry Co., Ltd.) and dopamine (A0305, Tokyo Chemical Industry Co., Ltd.) as catecholamine were sequentially added to final concentrations of from 10 nM to 100 µm.

The change in surface potential of the gold electrode with a polydopamine thin film layer is shown in FIG. 5, and the change in surface potential of the gold electrode without a polydopamine thin film layer is shown in FIG. 6. The vertical axes of FIGS. 5 and 6 show the change in surface potential of the molecular identifier component (mV), and the horizontal axes show the measurement time (seconds).

As shown in FIG. 5, the gold electrode with a polydopamine thin film layer did not respond to each catecholamine (dopamine or adrenaline). On the other hand, as shown in FIG. 6, the gold electrode without a polydopamine thin film layer reacted to each catecholamine (dopamine or adrenaline), and the gate surface potential changed concentration-dependently.

In other words, it was shown that by employing the gold electrode with a polydopamine thin film layer as an extended-gate electrode, non-specific adsorption of substances not targeted for detection to the gold electrode can be prevented, and noise during measurement could be reduced.

(4) Production of Biosensor that Selectively Detects Detection Target Substance (4-1) Formation of Molecular Imprinted Polymer (MIP) Layer that Selectively Captures Dopamine by ATRP Method (Manufacture Example 1)

Next, by the method shown below, an ultrathin film molecular imprinted polymer layer having formed therein a molecular imprint having a structure complementary to the molecular structure of dopamine was formed on the gold electrode produced in (2).

By immersing the gold electrode having a polydopamine thin film layer formed thereon in 1 mM 2-bromoisobutyrate (From Tokyo Chemical Industry Co., Ltd.)/ethanol solution overnight, polymerization initiator molecules were bound onto the polydopamine thin film layer.

Next, 0.02 g of 3-acrylamide phenylboronic acid, 0.05 g of N-3-(dimethylamino)propylmethacrylamide, 0.23 g of ethylene glycol dimethacrylate, and 0.02 g of dopamine were adjusted to a total of 0.6 g with ultrapure water, and then 0.4 g of dimethylformamide was added. This was completely dissolved, and then 100 μl of 10 mM copper (II) bromide and 100 mM Tris(2-pyridylmethyl)amine/dimethylformamide solution were added, followed by addition of 50 μl of 200 mM ascorbic acid.

To the gold electrode having polymerization initiator molecules bound thereto covered by a glass ring, 500 μl of the above solution (monomer solution) was added dropwise, and this was subjected to polymerization reaction under vacuum at 40° C. for 18 hours to produce a hydrogel on the gold electrode. Once the polymerization reaction was complete, the gate electrode was immersed in 0.1 M hydrochloric acid/methanol solution for 2 days in order to remove the monomer component and dopamine, thus forming an ultrathin film polymer layer having a molecular imprint complementary to the molecular structure of catecholamine on the gold gate electrode.

Measurement of the thickness of the polymer layer produced with an atomic force microscope (AFM) gave approximately 50 nm.

Moreover, with a method similar to the above, an ultrathin film molecular imprinted polymer (MIP) layer was also formed on the gold electrode without coating with polycatecholamine produced in (2).

(4-2) Formation of Molecular Imprinted Polymer (MIP) Layer that Selectively Captures Dopamine by ATRP Method (Manufacture Example 2)

As shown below, with the ethylene glycol dimethacrylate (cross-linking agent) condition different from (4-1), a molecular imprinted polymer (MIP) layer was formed on the gold electrode produced in (2). In Manufacture example 2, a more rigid polymer is formed since the proportion of ethylene glycol dimethacrylate (cross-linking agent) in the polymer solution is higher than that in Manufacture example 1.

By immersing the gold electrode having a polydopamine thin film layer formed thereon in 1 mM 2-bromoisobutyrate (From Tokyo Chemical Industry Co., Ltd.)/ethanol solution overnight, polymerization initiator molecules were bound onto the polydopamine thin film layer.

Next, 0.02 g of 3-acrylamide phenylboronic acid, 0.05 g of N-3-(dimethylamino)propylmethacrylamide, 0.43 g of ethylene glycol dimethacrylate, and 0.02 g of dopamine were adjusted to a total of 0.6 g with ultrapure water, and then 0.4 g of dimethylformamide was added. This was completely dissolved, and then 100 μl of 10 mM copper (II) bromide and 100 mM Tris(2-pyridylmethyl)amine/dimethylformamide solution were added, followed by addition of 50 μl of 200 mM ascorbic acid.

To the gold electrode having polymerization initiator molecules bound thereto covered by a glass ring, 500 μl of the above solution (monomer solution) was added dropwise, and this was subjected to polymerization reaction under vacuum at 40° C. for 6 hours to produce a hydrogel on the gold electrode. Once the polymerization reaction was complete, the gate electrode was immersed in 0.1 M hydrochloric acid/methanol solution for 2 days in order to remove the monomer component and dopamine, thus forming an ultrathin film polymer layer having a molecular imprint complementary to the molecular structure of catecholamine on the gold gate electrode.

Measurement of the thickness of the polymer layer produced with an atomic force microscope (AFM) gave approximately 50 nm.

Moreover, with a method similar to the above, an ultrathin film molecular imprinted polymer (MIP) layer was also formed on the gold electrode without coating with polycatecholamine produced in (2).

(4-3) Formation of Molecular Imprinted Polymer (MIP) Layer that Selectively Captures Dopamine by ATRP Method (Manufacture Example 3)

In this Manufacture example, as shown below, by allowing the polydopamine thin film layer comprising polymerization initiator molecules of the ATRP method to form in the step of forming the polydopamine thin film layer, an example of omitting the step of binding the polymerization initiator molecules in the step of allowing the formation of the molecular imprinted polymer layer is shown.

Dopamine powder 0.2 g, 0.49 g of 2-bromoisobutyryl bromide (From Tokyo Chemical Industry Co., Ltd.), and 0.21 g of triethylamine were dissolved in 10 ml of dimethylformamide, and this was stirred under nitrogen atmosphere for 4 hours. This was then mixed with 111 mM trishydroxymethylaminomethane solution, 500 μl of this solution was placed in the aforementioned gold base plate having a glass ring fixed thereon, and this was left standing at room temperature for 24 hours to allow formation of a polydopamine thin film layer with butyl groups (polymerization initiator molecules) introduced onto the gold base plate.

Next, 0.4 g of N-3-(dimethylamino)propylmethacrylamide, 0.6 g of 4-vinylphenylboronic acid, 0.6 g of ethylene glycol dimethacrylate, and 0.4 g of dopamine were dissolved in 4 ml of dimethylformamide and 2 ml of ultrapure water, and then 600 μl of mM copper (II) bromide and 100 mM Tris(2-pyridylmethyl)amine/dimethylformamide solution were added, followed by addition of 600 µl of 100 mM ascorbic acid to obtain the polymerization solution.

To the gold electrode coated with the polydopamine thin film layer comprising polymerization initiator molecules covered by a glass ring, 500 µl of the above solution (monomer solution) was added dropwise, and this was subjected to ATRP polymerization reaction under nitrogen atmosphere at room temperature for 18 hours to produce a hydrogel on the gold electrode. Once the polymerization reaction was complete, the gate electrode was immersed in 0.1 M hydrochloric acid/methanol solution for 2 days in order to remove the monomer component and dopamine, thus forming an ultrathin film polymer layer having a molecular imprint complementary to the molecular structure of dopamine on the gold gate electrode.

Measurement of the thickness of the polymer layer produced with an atomic force microscope (AFM) gave approximately 20 nm.

As a Comparative Example, with a composition same as the above polymerization solution except that dopamine was removed, hydrogel without molecular imprint was produced on the gold electrode by a similar method. Moreover, as another Comparative Example, an electrode of the gold electrode coated only with a polydopamine thin film layer with bromo groups introduced (i.e. electrode without molecular imprinted polymer layer) was prepared.

(4-4) Formation of Molecular Imprinted Polymer (MIP) Layer that Selectively Captures Glucose by ATRP Method (Manufacture Example 4)

In this Manufacture example, an example of producing an ultrathin film molecular imprinted polymer layer having a molecular structure complementary to the molecular structure of glucose is shown.

L-DOPA powder 0.2 g, 0.49 g of 2-bromoisobutyryl bromide (From Tokyo Chemical Industry Co., Ltd.), and 0.21 g of triethylamine were dissolved in 10 ml of dimethylformamide, and this was stirred under nitrogen atmosphere for 4 hours. This was then mixed with 111 mM trishydroxymethylaminomethane solution, 500 µl of this solution was placed in the aforementioned gold base plate having a glass ring fixed thereon, and this was left standing at room temperature for 24 hours to allow formation of a poly L-DOPA thin film layer with butyl groups introduced onto the gold base plate.

Next, 70 mM N-3-(dimethylamino)propylmethacrylamide, 70 mM 4-vinylphenylboronic acid, 280 mM hydroxyethyl methacrylate, 70 mM N',N'-methylenebisacrylamide, and 35 mM glucose were dissolved in 30 ml of dimethylformamide and 30 ml of ultrapure water, and then 1.4 mM copper (II) bromide and 14 mM Tris(2-pyridylmethyl)amine/dimethylformamide were added, followed by addition of 14 mM ascorbic acid to obtain the polymerization solution.

To the gold electrode coated with the poly L-DOPA thin film layer comprising polymerization initiator molecules covered by a glass ring, 500 µl of the above solution (monomer solution) was added dropwise, and this was subjected to ATRP polymerization reaction under nitrogen atmosphere at room temperature for 18 hours to produce a hydrogel on the gold electrode. Once the polymerization reaction was complete, the gate electrode was immersed in 0.1 M hydrochloric acid/methanol solution for 2 days in order to remove the monomer component and glucose, thus forming an ultrathin film polymer layer having a molecular structure complementary to the molecular structure of glucose on the gold gate electrode.

Measurement of the thickness of the polymer layer produced with an atomic force microscope (AFM) gave approximately 20 nm.

(5) Highly Sensitive Detection of Catecholamine by the Sensor of the Present Invention (Manufacture Example 1)

With the biosensor which is one embodiment of the present invention produced by the method of the above (1)-(4), the change in the gate surface potential of the gold electrode when dopamine and adrenaline were added as test samples as well as when L-DOPA (precursor of dopamine, adrenaline, and noradrenaline) was added were measured.

As shown in FIG. 7, with the sensor comprising a polydopamine thin film layer and a molecular imprinted polymer layer produced with the method of Manufacture example 1, changes in the gate surface potential when dopamine and adrenaline were added were seen in the negative direction from 10 nM. On the other hand, there was barely any change in the amount of change in the gate surface potential when L-DOPA was added. In other words, it was shown that the biosensor produced by the method of Manufacture example 1 can distinguishably detect dopamine and adrenaline from L-DOPA which is a precursor thereof.

The amount of change in the gate surface potential when adding each substance at concentrations from 10 nM to 1 µm is shown in FIG. 8. As shown in FIG. 8, it was shown that the biosensor produced by the method of Manufacture example 1 may distinguishably detect active catecholamines (dopamine and adrenaline) from the precursor thereof (L-DOPA) at an extremely low concentration range of catecholamine concentration such as those contained in saliva or urine. Note that it is reported that ordinarily, catecholamine is contained at a concentration of about a few hundred nM in saliva, about a few mM in urine, about a few µm in lacrimal fluid, and about a few nM in blood.

In other words, it was shown that the biosensor of the present invention is a device with superior practicality having high selectivity and sufficient detection sensitivity against trace amounts of biomolecules contained in various body fluids.

(6) Highly Sensitive Detection of Catecholamine by the Sensor of the Present Invention (Manufacture Example 2)

An experiment similar to (5) was performed with the biosensor produced by the method of Manufacture example 2. The results are shown in FIGS. 9 and 10.

As shown in FIGS. 9 and 10, with the sensor comprising a polydopamine thin film layer and a molecular imprinted polymer layer produced with the method of Manufacture example 2, significant change in gate surface potential was seen when dopamine was added. On the other hand, there was barely any change in the amount of change in the gate surface potential when adrenaline and L-DOPA were added. In other words, it was shown that the biosensor produced by the method of Manufacture example 2 can distinguishably detect dopamine from other catecholamines.

In other words, it was shown that the biosensor of the present invention can have further increased detection specificity against detection target substance by adjusting the rigidity of the molecular imprinted polymer layer.

(7) Highly Sensitive Detection of Dopamine by the Sensor of the Present Invention (Manufacture Example 3)

With the biosensor which is one embodiment of the present invention produced by the above method of Manufacture example 3 as well as Comparative Example, the change in the gate surface potential of the gold electrode when dopamine was added as the test sample was measured.

As shown in FIG. 11, in the sensor comprising a polydopamine thin film layer and a molecular imprinted polymer layer produced with the method of Manufacture example 3, significant change in gate surface potential was seen when dopamine was added. On the other hand, no change in gate surface potential was seen for the electrode having only the polydopamine thin film layer with bromo groups introduced. Moreover, it became clear that the range of change in gate surface potential when dopamine was added for the sensor without molecular imprint was extremely small compared to the sensor of the present invention.

In other words, it was shown that by employing the sensor of the present invention, extremely small amounts of catecholamine (e.g. catecholamine in the concentration range such as those contained in saliva or urine) can be selectively detected.

(8) Detection of Glucose by the Sensor of the Present Invention (Manufacture Example 4)

With the biosensor which is one embodiment of the present invention produced by the method of Manufacture example 4 above, the change in the gate surface potential of the gold electrode when dopamine was added as the test sample was measured.

The result of adding each of 400 μm, 1 mM, 4 mM, and 10 mM of glucose to the sensor comprising the poly L-DOPA thin film layer and the molecular imprinted polymer layer produced in the method of Manufacture example 4 is shown in Figure. As shown in FIG. 12, at each added concentration, significant change in gate surface potential was seen. Moreover, as shown in FIG. 13, when plotting the amount of shift in gate surface potential when each concentration of glucose was added was plotted, the gate surface potential changed glucose concentration-dependently with a correlation coefficient of 0.943.

In other words, it was shown that by employing the sensor of the present invention, extremely small amounts of glucose (e.g. glucose in the concentration range such as those contained in blood or urine) can be quantitatively detected.

In other words, it was shown that by employing the sensor of the present invention, various types of trace amount molecules may be quantitatively detected.

DESCRIPTION OF SYMBOLS

100: Gate electrode extended ion-sensitive sensor
101: Electric signal detector (MOSFET)
102: Electric wiring
103: Base plate
104: Ion-sensitive electrode (gold electrode)
105: Polycatecholamine thin film layer
106: Reference electrode
107: Buffer
108: Gate electrode
200: Gate electrode extended biosensor
201: FET device
202: Oxide gate insulator
203: Gate electrode
204: Electric wiring
205: Base plate
206: Extended-gate electrode (gold electrode)
207: Polycatecholamine thin film layer
208: Molecular imprinted polymer layer
209: Reference electrode
210: Buffer

The invention claimed is:

1. A biosensor comprising an identifier substance that can selectively bind to a detection target substance, and an electrode that takes a charge of said identifier substance, wherein the biosensor detects a change in charge density of said electrode generated by the selective binding of said detection target substance with said identifier substance,
    wherein a surface of said electrode is coated with polycatecholamine and all or a part of said electrode surface coated with polycatecholamine further has a polymer layer formed thereon, and wherein the polymer layer has a molecular imprint formed therein having a structure complementary to a molecular structure of the detection target substance,
    wherein said polymer layer comprises said identifier substance and has a thickness of 1 μm or less, and
    wherein said detection target substance is a catecholamine and said biosensor substantially does not detect L-DOPA.

2. The biosensor according to claim 1, wherein said polycatecholamine comprises at least one of L-DOPA, dopamine, adrenaline, and noradrenaline polymer.

3. The biosensor according to claim 1, wherein said polymer layer has a thickness of 100 nm or less.

4. The biosensor according to claim 1, wherein said detection target substance is dopamine, adrenaline, or noradrenaline.

5. The biosensor according to claim 1, wherein said identifier substance is phenylboronic acid.

6. The biosensor according to claim 1, wherein said electrode is a gold electrode, a silver electrode, a copper electrode, a platinum electrode, an indium-tin oxide (ITO) electrode, a palladium electrode, a steel electrode, a nickel titanium alloy electrode, a titanium oxide electrode, a silicon dioxide electrode, a crystal electrode, an aluminum oxide electrode, a gallium arsenide electrode, a glass electrode, or a tantalum oxide electrode.

7. The biosensor according to claim 1, wherein said electrode is electrically connected to the gate electrode of a field effect transistor.

8. The biosensor according to claim 7, wherein said electrode is placed away from said field effect transistor, and and said electrode is electrically connected to said gate electrode of said field effect transistor via electric wiring.

9. The biosensor according to claim 7, wherein said electrode is electrically connected to said gate insulator film by being directly mounted on the gate insulator film of said field effect transistor.

10. The biosensor according to claim 1, wherein said electrode is electrically connected to a signal amplifier.

11. The biosensor according to claim 10, wherein said signal amplifier is an operational amplifier.

12. The biosensor according to claim 1, wherein said polymer layer is formed by a method comprising:
    (a) polymerizing a monomer solution comprising one or more types of monomers, said detection target substance, and said identifier substance on all or a part of the surface of said electrode to allow formation of the polymer layer on all or a part of the surface of said electrode, and then (b) removing said detection target substance from said polymer layer to allow formation of the molecular imprint having a structure complementary to the molecular structure of said detection target substance on said polymer layer.

13. The biosensor according to claim 12, wherein the polymerization of said monomer solution is living radical polymerization or electrolytic polymerization.

14. The biosensor according to claim 13, wherein said living radical polymerization is atom transfer radical polymerization (ATRP), reversible addition/fragmentation chain transfer polymerization (RAFT), or nitroxide-mediated polymerization (NMP).

15. The biosensor according to claim 14, wherein said living radical polymerization is atom transfer radical polymerization (ATRP), and prior to said step (a), polymerization initiator molecules are bound to all or a part of the electrode surface.

16. The biosensor according to claim 12, wherein said step (a) includes applying a monomer solution comprising one or more types of monomers, said detection target substance, and said identifier substance to all or a part of the electrode surface with a spin coat, and polymerizing the applied monomer solution to allow formation of the polymer layer on all or a part of the surface of said electrode.

17. The biosensor according to claim 12, wherein said monomer solution comprises at least one monomer selected from the group consisting of acrylamide derivative, methacrylamide derivative, acrylate derivative, methacrylate derivative, acrylonitrile, 2-vinylpyridine, 4-vinylpyridine, N-vinyl-2-pyrrolidone, and vinyl acetate.

18. The biosensor according to claim 1, wherein the detection target substance and the identifier substance are respectively (a) dopamine and phenylboronic acid, or (b) dopamine and a monomer having an amino group.

19. An electrode used in a biosensor, characterized in that:

said biosensor is a biosensor that detects a change in charge density of said electrode generated by selective binding of a detection target substance with an identifier substance, said electrode is an electrode that takes a charge of said identifier substance that can bind to said detection target substance, a surface of said electrode is coated with polycatecholamine, all or a part of the surface of said electrode coated with polycatecholamine further comprises a polymer layer formed thereon, and the polymer layer has a molecular imprint formed therein having a structure complementary to the molecular structure of the detection target substance, wherein said detection target substance is a catecholamine and said biosensor substantially does not detect L-DOPA, said polymer layer comprises said identifier substance, and said polymer layer has a thickness of 1 μm or less.

* * * * *